(12) United States Patent
Hofgen et al.

(10) Patent No.: US 7,067,536 B2
(45) Date of Patent: Jun. 27, 2006

(54) 4-,6- OR 7-HYDROXYINDOLES WITH N-OXIDE GROUPS AND THE USE THEREOF AS THERAPEUTIC AGENTS

(75) Inventors: Nobert Hofgen, Ottendorf-Okrilla (DE); Hildegard Kuss, Dresden (DE); Karin Steinike, Radebeul (DE); Ute Egerland, Radebeul (DE); Chris Rundfeldt, Coswig (DE)

(73) Assignee: Elbion AG, Radebeul (DE)

( * ) Notice: Subject to any disclaimer, the term of this patent is extended or adjusted under 35 U.S.C. 154(b) by 25 days.

(21) Appl. No.: 10/825,862

(22) Filed: Apr. 16, 2004

(65) Prior Publication Data

US 2004/0242643 A1  Dec. 2, 2004

(30) Foreign Application Priority Data

Apr. 24, 2003  (DE) ................. 103 18 611

(51) Int. Cl.
*A61K 31/4439* (2006.01)
*C07D 401/12* (2006.01)

(52) U.S. Cl. ........................ 514/339; 546/278.1
(58) Field of Classification Search ............. 546/278.1; 514/339
See application file for complete search history.

(56) References Cited

U.S. PATENT DOCUMENTS

| 6,232,327 B1 | 5/2001 | Nickel et al. |
| 6,251,923 B1 | 6/2001 | Hofgen et al. |
| 6,432,987 B1 * | 8/2002 | Gunther et al. ............. 514/339 |
| 2002/0111351 A1 | 8/2002 | Hofgen et al. |
| 2002/0115651 A1 | 8/2002 | Hofgen et al. |
| 2002/0119971 A1 | 8/2002 | Hofgen et al. |
| 2002/0137745 A1 | 9/2002 | Hofgen et al. |
| 2003/0134876 A1 | 7/2003 | Hofgen et al. |
| 2003/0153759 A1 | 8/2003 | Koya et al. |
| 2003/0195360 A1 | 10/2003 | Nickel et al. |
| 2003/0204090 A1 | 10/2003 | Chimmanamada, et al. |
| 2004/0116462 A1 | 6/2004 | Ono et al. |
| 2004/0147759 A1 * | 7/2004 | Hofgen et al. ............. 548/181 |
| 2004/0266760 A1 * | 12/2004 | Hofgen et al. ........... 514/227.5 |

FOREIGN PATENT DOCUMENTS

| DE | 196 36 150 A | 3/1998 |
| DE | 198 14 838 A | 10/1999 |
| WO | WO-99/55696 A | 11/1999 |

OTHER PUBLICATIONS

Orally Active Indole N-oxide . . . inhibitors, Hulme, et al. Bioorganic & Medicinal Chem. Letters. (1998).
Anti-Inflammatory and Immunomodulatory . . . In Vitro, Hatzelmann, et al. Journ. Of Pharmacology and Experimental Therapeutics. Vo.. 297. (2001).

* cited by examiner

*Primary Examiner*—Patricia L. Morris
(74) *Attorney, Agent, or Firm*—Fulbright & Jaworski L.L.P.

(57) ABSTRACT

The invention relates to substituted 4-, 6- or 7-hydroxyindoles with N-oxide groups, process for their preparation, pharmaceutical preparations which comprise these compounds, and the pharmaceutical use of these compounds, which are inhibitors of phosphodiesterase 4, as active ingredients for the treatment of disorders which can be influenced by inhibition of phosphodiesterase 4 activity in particular in immunocompetent cells (e.g. macrophages and lymphocytes) by the compounds of the invention.

7 Claims, No Drawings

4-,6- OR 7-HYDROXYINDOLES WITH N-OXIDE GROUPS AND THE USE THEREOF AS THERAPEUTIC AGENTS

BACKGROUND AND SUMMARY OF THE INVENTION

This application claims priority from German Patent Application 103 18 611.5 filed Apr. 24, 2003. hereby incorporated by reference in its entirety.

The invention relates to substituted 4-,6- or 7-hydroxyindoles with N-oxide groups, process for their preparation, pharmaceutical preparations which comprise these compounds, and the pharmaceutical use of these compounds, which are inhibitors of phosphodiesterase 4, as active ingredients for the treatment of disorders which can be influenced by inhibition of phosphodiesterase 4 activity in particular in immunocompetent cells (e.g. macrophages and lymphocytes) by the compounds of the invention.

Activation of cell membrane receptors by transmitters leads to activation of the second messenger system. Adenylate cyclase synthesizes the active cyclic AMP (cAMP) and cyclic GMP (cGMP) respectively from AMP and GMP. cAMP and cGMP lead for example in smooth muscle cells to relaxation, and in inflammatory cells to inhibition of mediator release and mediator synthesis. The second messengers cAMP and cGMP are degraded by phosphodiesterases (PDE). To date, 11 families of PDE enzymes (PDE1–11) are known and differ through their substrate specificity (cAMP, cGMP or both) and the dependence on other substrates (e.g. calmodulin). These isoenzymes have different functions in the body and are expressed differently in individual cell types (Beavo, J. A., Conti, M. and Heaslip, R. J., Multiple cyclic nucleotide phosphodiesterases. Mol. Pharmacol. 1994, 46:399–405; Hall, I. P., Isoenzyme selective phosphodiesterase inhibitors: potential clinical uses, Br. J. clin. Pharmacol. 1993, 35:1–7). Inhibition of the various PDE isoenzyme types results in accumulation of cAMP or cGMP in cells, which can be utilized therapeutically (Torphy, T. J., Livi, G. P., Christensen, S. B. Novel Phosphodiesterase Inhibitors for the Therapy of Asthma, Drug News and Perspectives 1993, 6:203–214).

The predominant PDE-isoenzyme in cells important for allergic inflammations (lymphocytes, mast cells, eosinophilic granulocytes, macrophages) is that of type 4 (Torphy, J. T. and Undem, B. J., Phosphodiesterase inhibitors: new opportunities for the treatment of asthma. Thorax 1991, 46:512–523). Inhibition of PDE 4 by suitable inhibitors is therefore regarded as an important approach to the therapy of a large number of allergically induced disorders (Schudt, Ch., Dent, G., Rabe, K, Phosphodiesterase Inhibitors, Academic Press London 1996).

An important property of phosphodiesterase 4 inhibitors is inhibition of the release of tumor necrosis factor α (TNFα) from inflammatory cells. TNFα is an important proinflammatory cytokine which influences a large number of biological processes. TNFα is released for example from activated macrophages, activated T lymphocytes, mast cells, basophils, fibroblasts, endothelial cells and astrocytes in the brain. It has itself an activating effect on neutrophils, eosinophils, fibroblasts and endothelial cells, whereby various tissue-damaging mediators are released. The effect of TNFα in monocytes, macrophages and T lymphocytes is increased production of further proinflammatory cytokines such as GM-CSF (granulocyte-macrophage colony-stimulating factor) or interleukin-8. Owing to its proinflammatory and catabolic effect, TNFα plays a central role in a large number of disorders such as inflammations of the respiratory tract, inflammations of the joints, endotoxic shock, tissue rejections, AIDS and many other immunological disorders. Thus, phosphodiesterase 4 inhibitors are likewise suitable for the therapy of such disorders associated with TNFα.

Chronic obstructive pulmonary diseases (COPD) are widespread in the population and also have great economic importance. Thus, COPD disorders are the cause of about 10–15% of all illness costs in the developed countries, and about 25% of all deaths in the USA are attributable to this cause (Norman, P.: COPD: New developments and therapeutic opportunities, Drug News Perspect. 11 (7), 431–437, 1998). The WHO estimates that COPD will become the third-commonest cause of death in the next 20 years.

The pathological condition of chronic obstructive pulmonary diseases (COPD) encompasses various pathological conditions of chronic bronchitis with the symptoms of coughing and expectoration, and progressive and irreversible deterioration in lung function (expiration is particularly affected). The course of the disease is episodic and often complicated by bacterial infections (Rennard, S. I.: COPD: Overview of definitions, Epidemiology, and factors influencing its development. Chest, 113 (4) Suppl., 235S–241S, 1998). There is a steady decline in lung function during the disorder, the lung becomes increasingly emphysematous, and the patients' breathing difficulty becomes obvious. This disorder markedly impairs the patients' quality of life (shortness of breath, low exercise tolerance) and significantly shortens their life expectancy. Besides environmental factors, the main risk factor is smoking (Kummer, F.: Asthma and COPD. Atemw.-Lungenkrkh. 20 (5), 299–302, 1994; Rennard, S. I.: COPD: Overview of definitions, Epidemiology, and factors influencing its development. Chest, 113 (4) Suppl., 235S–241S, 1998) and thus men are affected distinctly more frequently than are women. However, this picture will change in the future due to the alteration in lifestyles and the increase in the number of female smokers.

Current therapy claims only to alleviate the symptoms without affecting the causes of the progression of the disorder. The use of long-acting beta2 agonists (e.g. salmeterol), possibly in combination with muscarinergic antagonists (e.g. ipratropium), improves lung function through bronchodilatation and is routinely employed (Norman, P.: COPD: New developments and therapeutic opportunities, Drug News Perspect. 11 (7), 431–437, 1998). Bacterial infections play a large part in the episodes of COPD and need antibiotic treatment (Wilson, R.: The role of infection in COPD, Chest, 113 (4) Suppl., 242S–248S, 1998; Grossman, R. F.: The value of antibiotics and the outcomes of antibiotic therapy in exacerbations of COPD. Chest, 113 (4) Suppl., 249S–255S, 1998). Therapy of this disorder is currently unsatisfactory, especially in relation to the continuous decline in lung function. New therapeutic approaches acting on mediators of inflammation, proteases or adhesion molecules might be very promising (Barnes, P. J.: Chronic obstructive disease: new opportunities for drug development, TiPS 10 (19), 415–423, 1998).

Irrespective of the bacterial infections complicating the disorder, a chronic inflammation is found in the bronchi and is dominated by neutrophilic granulocytes. The mediators and enzymes released by neutrophilic granulocytes are thought inter alia to be responsible for the observed structural changes in the respiratory tract (emphysema). Inhibition of the activity of neutrophilic granulocytes is thus a rational approach to the prevention or slowing down of the progression of COPD (deterioration in parameters of lung function). An important stimulus for the activation of granulocytes is the proinflammatory cytokine TNFα (tumor necrosis factor). Thus, it is known that TNFα stimulates the formation of oxygen free radicals by neutrophilic granulocytes (Jersmann, H. P. A.; Rathjen, D. A. and Ferrante, A.: Enhancement of LPS-induced neutrophil oxygen radical production by TNFα, Infection and Immunity, 4, 1744–1747, 1998). PDE4 inhibitors are able to inhibit very effectively the release of TNFα from a large number of cells and thus suppress the activity of neutrophilic granulocytes. The nonspecific PDE inhibitor pentoxifylline is able to inhibit both the formation of oxygen free radicals and the phagocytic ability of neutrophilic granulocytes (Wenisch, C.; Zedtwitz-Liebenstein, K.; Parschalk, B. and Graninger, W.: Effect of pentoxifylline in vitro on neutrophil reactive oxygen production and phagocytic ability assessed by flow cytometry, Clin. Drug Invest., 13(2):99–104, 1997).

Various PDE 4 inhibitors have already been disclosed. These are primarily xanthine derivatives, rolipram analogs or nitraquazone derivatives (review in: Karlsson, J. A., Aldos, D., Phosphodiesterase 4 inhibitors for the treatment of asthma, Exp. Opin. Ther. Patents 1997, 7:989–1003). It has not been possible to date for any of these compounds to be used clinically. It was unavoidably found that the known PDE4 inhibitors also have various side effects, such as nausea and emesis, which it has not to date been possible to suppress adequately. It is therefore necessary to discover novel PDE4 inhibitors with improved therapeutic index.

Indol-3-ylglyoxylamides and processes for preparing them have already been described several times. In all cases, indoles unsubstituted in position 3, which are synthesized by substitution in position 1 of a commercially available indole, were converted by reaction with oxalyl halides into indol-3-ylglyoxylyl halides which subsequently afford, by reaction with ammonia or with primary or secondary amines, the corresponding indol-3-ylglyoxylamides. (Scheme 1)

Scheme 1:

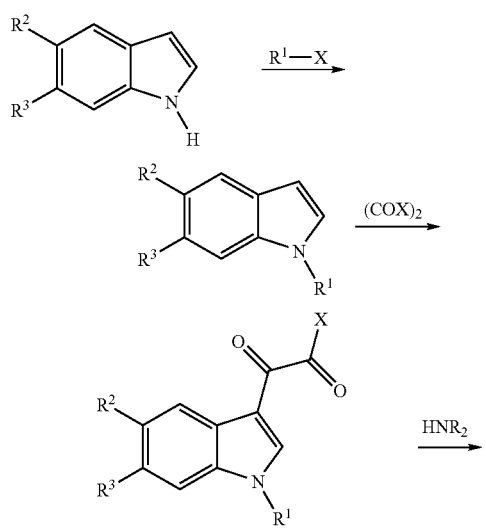

X = halogen

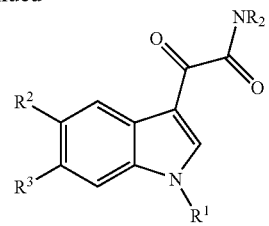

Thus, U.S. Pat. Nos. 2,825,734 and 3,188,313 describe various indol-3-ylglyoxylamides which are prepared by the manner depicted in Scheme 1. These compounds were used as intermediates for preparing indole derivatives produced by reductions. U.S. Pat. No. 3,642,803 also describes indol-3-ylglyoxylamides.

The preparation of 5-methoxyindol-3-ylglyoxylamides is described in *Farmaco* 22 (1967), 229–244. Again there is reaction of the indole derivative used with oxalyl chloride, and the resulting indol-3-ylglyoxylyl chloride is reacted with an amine.

In addition, U.S. Pat. No. 6,008,231 describes indol-3-ylglyoxylamides and processes for preparing them. Once again, the reaction steps and conditions depicted in Scheme 1 are used.

Substituted 5-hydroxyindolylglyoxylamides and 6-hydroxyindolylglyoxylamides and processes for preparing them and the use thereof as PDE4 inhibitors were described for the first time in patent application DE 198 18 964 A1.

7-Azaindol-3-ylglyoxylamides are disclosed as PDE4 inhibitors in patent application DE 100 53 275 A1, which also describes their preparation and use as therapeutic agents.

4- and 7-Hydroxyindole derivatives, their preparation and use as PDE4 inhibitors are proposed in patent application DE 102 53 426.8.

The invention relates to substituted hydroxyindoles of the general formula 1

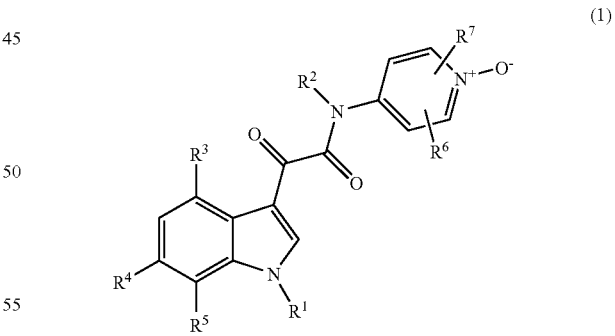

(1)

in which

R¹
(i) is —C$_{1-10}$-alkyl, straight-chain or branched-chain, optionally mono- or polysubstituted by —OH, —SH, —NH$_2$, —NHC$_{1-6}$-alkyl, —N(C$_{1-6}$-alkyl)$_2$, —NHC$_{6-14}$-aryl, —N(C$_{6-14}$-aryl)$_2$, —N(C$_{1-6}$-alkyl) (C$_{6-14}$-aryl), —NO$_2$, —CN, —F, —Cl, —Br, —I, —O—C$_{1-6}$-alkyl, —O—$C_{6-14}$-aryl, —S—$C_{1-6}$-alkyl, —S—$C_{6-14}$-aryl, —$SO_3H$, —$SO_2C_{1-6}$-alkyl, —$SO_2C_{6-14}$-aryl, —$OSO_2$ $C_{1-6}$-alkyl, —$OSO_2C_{6-14}$-aryl, —COOH, —(CO)$C_{1-5}$-alkyl, —COO—$C_{1-5}$-alkyl, —O(CO)$C_{1-5}$-alkyl, by mono-, bi- or tricyclic saturated or mono- or polyunsaturated carbocycles with 3–14 ring members or/and by mono-, bi- or tricyclic saturated or mono- or polyunsaturated heterocycles with 5–15 ring members and 1–6 heteroatoms, which are preferably N, O and S, wherein the $C_{6-14}$-aryl groups and the carbocyclic and heterocyclic substituents in turn may optionally be substituted one or more times by —$C_{1-6}$-alkyl, —OH, —$NH_2$, —$NHC_{1-6}$-alkyl, —$N(C_{1-6}$-alkyl$)_2$, —$NO_2$, —CN, —F, —Cl, —Br, —I, —O—$C_{1-6}$-alkyl, —S—$C_{1-6}$-alkyl, —$SO_3H$, —$SO_2C_{1-6}$-alkyl, —$OSO_2C_{1-6}$-alkyl, —COOH, —(CO)$C_{1-5}$-alkyl, —COO—$C_{1-5}$-alkyl or/and —O(CO)$C_{1-5}$-alkyl, and wherein the alkyl groups on the carbocyclic and heterocylic substituents in turn may optionally be substituted one or more times by —OH, —SH, —$NH_2$, —F, —Cl, —Br, —I, —$SO_3H$ or/and —COOH, or (ii) is —$C_{2-10}$-alkenyl, mono- or polyunsaturated, straight-chain or branched-chain, optionally mono- or polysubstituted by —OH, —SH, —$NH_2$, —$NHC_{1-6}$-alkyl, —$N(C_{1-6}$-alkyl$)_2$, —$NHC_{6-14}$-aryl, —$N(C_{6-14}$-aryl$)_2$, —$N(C_{1-6}$-alkyl)($C_{6-14}$-aryl) , —$NO_2$, —CN, —F, —Cl, —Br, —I, —O—$C_{1-6}$-alkyl, —O—$C_{6-14}$-aryl, —S—$C_{1-6}$-alkyl, —S—$C_{6-14}$-aryl, —$SO_3H$, —$SO_2C_{1-6}$-alkyl, —$SO_2C_{6-14}$-aryl, —$OSO_2C_{1-6}$-alkyl, —$OSO_2C_{6-14}$-aryl, —COOH, —(CO)$C_{1-5}$-alkyl, —COO—$C_{1-5}$-alkyl, —O(CO)$C_{1-5}$-alkyl, by mono-, bi- or tricyclic saturated or mono- or polyunsaturated carbocycles with 3–14 ring members or/and by mono-, bi- or tricyclic saturated or mono- or polyunsaturated heterocycles with 5–15 ring members and 1–6 heteroatoms, which are preferably N, O and S, wherein the $C_{6-14}$-aryl groups and the carbocyclic and heterocyclic substituents in turn may optionally be substituted one or more times by —$C_{1-6}$-alkyl, —OH, —$NH_2$, —$NHC_{1-6}$-alkyl, —$N(C_{1-6}$-alkyl$)_2$, —$NO_2$, —CN, —F, —Cl, —Br, —I, —O—$C_{1-6}$-alkyl, —S—$C_{1-6}$-alkyl, —$SO_3H$, —$SO_2C_{1-6}$-alkyl, —$OSO_2C_{1-6}$-alkyl, —COOH, —(CO)$C_{1-5}$-alkyl, —COO—$C_{1-5}$-alkyl or/and —O(CO)—$C_{1-5}$-alkyl, and wherein the alkyl groups on the carbocyclic and heterocyclic substituents in turn may optionally be substituted one or more times by —OH, —SH, —$NH_2$, —F, —Cl, —Br, —I, —$SO_3H$ or/and —COOH, $R^2$ is hydrogen or —$C_{1-3}$-alkyl, $R^3$, $R^4$ and $R^5$ are hydrogen or a hydroxyl group, wherein at least one of these substituents must be a hydroxyl group, $R^6$ and $R^7$ may be identical or different and are hydrogen, —$C_{1-6}$-alkyl, —OH, —SH, —$NH_2$, —$NHC_{1-6}$-alkyl, —$N(C_{1-6}$-alkyl$)_2$, —$NO_2$, —CN, —$SO_3H$, —$SO_3$—$C_{1-6}$-alkyl, —COOH, —COO—$C_{1-6}$-alkyl, —O(CO)—$C_{1-5}$-alkyl, —F, —Cl, —Br, —I, —O—$C_{1-6}$-alkyl, —S—$C_{1-6}$-alkyl, -phenyl or -pyridyl, wherein the phenyl or pyridyl substituents in turn may optionally be substituted one or more times by —$C_{1-3}$-alkyl, —OH, —SH, —$NH_2$, —$NHC_{1-3}$-alkyl, —$N(C_{1-3}$-alkyl$)_2$, —$NO_2$, —CN, —$SO_3H$, —$SO_3C_{1-3}$-alkyl, —COOH, —$COOC_{1-3}$-alkyl, —F, —Cl, —Br, —I, —O—$C_{1-3}$-alkyl, —S—$C_{1-3}$-alkyl, or/and —O(CO)$C_{1-3}$-alkyl, and wherein the alkyl substituents in turn may optionally be substituted one or more times by —OH, —SH, —$NH_2$, —F, —Cl, —Br, —I, —$SO_3H$, —$SO_3C_{1-3}$-alkyl, —COOH, —$COOC_{1-3}$-alkyl, —O—$C_{1-3}$-alkyl, —S—$C_{1-3}$-alkyl or/and —O(CO)—$C_{1-3}$-alkyl.

Preferred compounds of the formula 1 are those in which $R^1$ is an optionally substituted $C_{1-4}$-alkyl residue, particularly preferably a $C_1$ residue, with a cyclic substituent. The cyclic substituents are preferably $C_{3-8}$-cycloalkyl groups or $C_{5-6}$-aryl or heteroaryl residues which may have at least one substituent selected from halogen, i.e. —F, —Cl, —Br or —I, —OH, —$NO_2$, —CN and —$CF_3$.

Of the compounds of formula 1 the invention preferably relates to those compounds in which $R^2$ is hydrogen or a methyl group.

Of the compounds of formula 1 the invention preferably relates to those compounds in which $R^5$ is a hydroxyl group and $R^3$ and $R^4$ are hydrogen.

Of the compounds of formula 1 the invention preferably relates to those compounds in which at least one of $R^6$ or $R^7$ is a halogen atom. $R^6$ and $R^7$ are preferably partiularly halogen atoms. The compounds mentioned in the experimental examples are also particularly preferred.

The invention further relates to physiologically tolerated salts of the compounds of formula 1.

The physiologically tolerated salts are obtained in a conventional way by neutralizing the bases with inorganic or organic acids or by neutralizing the acids with inorganic or organic bases. Examples of suitable inorganic acids are hydrochloric acid, sulfuric acid; phosphoric acid or hydrobromic acid, and examples of suitable organic acids are carboxylic or sulfonic acids, such as acetic acid, tartaric acid, lactic acid, propionic acid, glycolic acid, malonic acid, maleic acid, fumaric acid, tannic acid, succinic acid, alginic acid, benzoic acid, 2-phenoxybenzoic acid, 2-acetoxybenzoic acid, cinnamic acid, mandelic acid, citric acid, malic acid, salicylic acid, 3-aminosalicylic acid, ascorbic acid, embonic acid, nicotinic acid, isonicotinic acid, oxalic acid, amino acids, methanesulfonic acid, ethanesulfonic acid, 2-hydroxyethanesulfonic acid, ethane-1,2-disulfonic acid, benzenesulfonic acid, 4-methylbenzenesulfonic acid or naphthalene-2-sulfonic acid. Examples of suitable inorganic bases are sodium hydroxide solution, potassium hydroxide solution, ammonia, and suitable organic bases are amines, but preferably tertiary amines such as trimethylamine, triethylamine, pyridine, N,N-dimethylaniline, quinoline, isoquinoline, α-picoline, β-picoline, γ-picoline, quinaldine or pyrimidine.

Physiologically tolerated salts of the compounds of formula 1 can additionally be obtained by converting derivatives having tertiary amino groups in a manner known per se with quaternizing agents into the corresponding quaternary ammonium salts. Examples of suitable quaternizing agents are alkyl halides such as methyl iodide, ethyl bromide and n-propyl chloride, but also arylalkyl halides such as benzyl chloride or 2-phenylethyl bromide.

The invention further relates to the D form, the L form and D,L mixtures of compounds of the formula 1 which contain an asymmetric carbon atom, and in the case of a plurality of asymmetric carbon atoms, also the diastereomeric forms. Compounds of the formula 1 which contain asymmetric carbon atoms and usually result as racemates can be separated into the optically active isomers in a manner known per se, for example with an optically active acid. However, it is also possible to employ an optically active starting substance from the outset, in which case a corresponding optically active or diastereomeric compound is obtained as final product.

The compounds of the invention have been found to have pharmacologically important properties which can be utilized in therapy. The compounds of formula 1 can be employed alone, in combination with one another or in combination with other active ingredients.

The compounds of the invention are inhibitors of phosphodiesterase 4. It is therefore an aspect of this invention that the compounds of formula 1 and the salts thereof, and pharmaceutical preparations which comprise these compounds or salts thereof, can be used for the treatment of disorders in which inhibition of phosphodiesterase 4 is beneficial.

These disorders include, for example, inflammations of joints, including arthritis and rheumatoid arthritis, and other arthritic disorders such as rheumatoid spondylitis and osteoarthritis. Further possible uses are the treatment of patients suffering from osteoporosis, sepsis, septic shock, Gram-negative sepsis, toxic shock syndrome, respiratory distress syndrome, asthma or other chronic pulmonary disorders, bone resorption disorders or transplant rejection reactions or other autoimmune diseases such as lupus erythematosus, multiple sclerosis, glomerulonephritis and uveitis, insulin-dependent diabetes mellitus and chronic demyelinization.

The compounds of the invention can additionally be employed for the therapy of infections such as viral infections and parasitic infections, for example for the therapy of malaria, leishmaniasis, infection-related fever, infection-related muscle pain, AIDS and cachexia, and of non-allergic rhinitis.

The compounds of the invention can likewise be used for the therapy of hyperproliferative disorders, in particular of cancers, for example for the therapy of melanomas, of breast cancer, lung cancer, bowel cancer, skin cancer and of leukemias.

The compounds of the invention can also be employed as bronchodilators and for the treatment of asthma, e.g. for asthma prophylaxis.

The compounds of formula 1 are in addition inhibitors of the accumulation of eosinophils and the activity thereof. Accordingly, the compounds of the invention can also be employed for disorders in which eosinophils are involved. These disorders include, for example, inflammatory respiratory tract disorders such as bronchial asthma, allergic rhinitis, allergic conjuctivitis, atopic dermatitis, eczemas, allergic angiitis, eosinophil-mediated inflammations such as eosinophilic fasciitis, eosinophilic pneumonia and PIE syndrome (pulmonary infiltration with eosinophilia), urticaria, ulcerative colitis, Crohn's disease and proliferative skin disorders such as psoriasis or keratosis.

It is an aspect of this invention that the compounds of formula 1 and salts thereof are also able to inhibit LPS-induced pulmonary neutrophilic infiltration in rats in vivo. The pharmacologically significant properties which have been found prove that the compounds of formula 1 and salts thereof, and pharmaceutical preparations which comprise these compounds or salts thereof, can be utilized therapeutically for the treatment of chronic obstructive pulmonary diseases.

The compounds of the invention additionally have neuroprotective properties and can be used for the therapy of diseases in which neuroprotection is beneficial. Examples of such disorders are senile dementia (Alzheimer's disease), memory loss, Parkinson's disease, depression, strokes and intermittent claudication.

Further possible uses of the compounds of the invention are the prophylaxis and therapy of prostate disorders such as, for example, benign prostate hyperplasia, pollakisuria, nocturia, and the treatment of incontinence, of colic induced by urinary calculi, and of male and female sexual dysfunctions.

Finally, the compounds of the invention can likewise be used to inhibit the development of drug dependence on repeated use of analgesics such as, for example, morphine, and to reduce the development of tolerance on repeated use of these analgesics.

The drug products are produced by using an effective dose of the compounds of the invention or salts thereof, in addition to conventional adjuvants, carriers and additives. The dosage of the active ingredients may vary depending on the route of administration, age and weight of the patient, nature and severity of the disorders to be treated and similar factors. The daily dose may be given as a single dose to be administered once a day, or divided into 2 or more daily doses, and is usually 0.001–100 mg. Daily dosages of 0.1–50 mg are particularly preferably administered.

Oral, parenteral, intravenous, transdermal, topical, inhalational and intranasal preparations are suitable as administration form. Topical, inhalational and intranasal preparations of the compounds of the invention are particularly preferably used. Conventional pharmaceutical presentations such as tablets, coated tablets, capsules, dispersible powders, granules, aqueous solutions, aqueous or oily suspensions, syrup, solutions or drops are used.

Solid drug forms may comprise inert ingredients and carriers such as, for example, calcium carbonate, calcium phosphate, sodium phosphate, lactose, starch, mannitol, alginates, gelatin, guar gum, magnesium stearate or aluminum stearate, methylcellulose, talc, colloidal silicas, silicone oil, high molecular weight fatty acids (such as stearic acid), agar-agar or vegetable or animal fats and oils, solid high molecular weight polymers (such as polyethylene glycol); preparations suitable for oral administration may, if desired, comprise additional flavorings and/or sweeteners.

Liquid drug forms can be sterilized and/or where appropriate comprise excipients such as preservatives, stabilizers, wetting agents, penetrants, emulsifiers, spreading agents, solubilizers, salts, sugars or sugar alcohols to control the osmotic pressure or for buffering and/or viscosity regulators.

Examples of such additives are tartrate buffer and citrate buffer, ethanol, complexing agents (such as ethylenediaminetetraacetic acid and its non-toxic salts). Suitable for controling the viscosity are high molecular weight polymers such as, for example, liquid polyethylene oxide, microcrystalline celluloses, carboxymethylcelluloses, polyvinylpyrrolidones, dextrans or gelatin. Examples of solid carriers are starch, lactose, mannitol, methylcellulose, talc, colloidal silicas, higher molecular weight fatty acids (such as stearic acid), gelatin, agar-agar, calcium phosphate, magnesium stearate, animal and vegetable fats, solid high molecular weight polymers such as polyethylene glycol.

Oily suspensions for parenteral or topical uses may be vegetable synthetic or semisynthetic oils such as, for example, liquid fatty acid esters with in each case 8 to 22 C atoms in the fatty acid chains, for example palmitic, lauric, tridecylic, margaric, stearic, arachic, myristic, behenic, pentadecylic, linoleic, elaidic, brasidic, erucic or oleic acid, which are esterified with monohydric to trihydric alcohols having 1 to 6 C atoms, such as, for example, methanol, ethanol, propanol, butanol, pentanol or isomers thereof, glycol or glycerol. Examples of such fatty acid esters are commercially available miglyols, isopropyl myristate, isopropyl palmitate, isopropyl stearate, PEG 6-capric acid, caprylic/capric esters of saturated fatty alcohols, polyoxyethylene glycerol trioleates, ethyl oleate, waxy fatty acid esters such as artificial duck preen gland fat, coco fatty acid isopropyl ester, oleyl oleate, decyl oleate, ethyl lactate, dibutyl phthalate, diisopropyl adipate, polyol fatty acid esters inter alia. Likewise suitable are silicone oils differing in viscosity or fatty alcohols such as isotridecyl alcohol, 2-octyldodecanol, cetylstearyl alcohol or oleyl alcohol, fatty acids such as, for example, oleic acid. It is additionally possible to use vegetable oils such as castor oil, almond oil, olive oil, sesame oil, cottonseed oil, peanut oil or soybean oil.

Suitable solvents, gel formers and solubilizers are water or water-miscible solvents. Suitable examples are alcohols such as, for example, ethanol or isopropyl alcohol, benzyl alcohol, 2-octyldodecanol, polyethylene glycols, phthalates, adipates, propylene glycol, glycerol, di- or tripropylene glycol, waxes, methyl Cellosolve, Cellosolve, esters, morpholines, dioxane, dimethyl sulfoxide, dimethylformamide, tetrahydrofuran, cyclohexanone etc.

Film formers which can be used are cellulose ethers able to dissolve or swell both in water and in organic solvents, such as, for example, hydroxypropylmethylcellulose, methylcellulose, ethylcellulose or soluble starches.

Combined forms of gel formers and film formers are likewise perfectly possible. Ionic macromolecules are used in particular for this purpose, such as, for example, sodium carboxymethylcellulose, polyacrylic acid, polymethacrylic acid and salts thereof, sodium amylopectin semiglycolate, alginic acid or propylene glycol alginate as sodium salt, gum arabic, xanthan gum, guar gum or carrageenan.

Further formulation aids which can be employed are: glycerol, paraffin of differing viscosity, triethanolamine, collagen, allantoin, novantisolic acid.

It may also be necessary to use surfactants, emulsifiers or wetting agents for the formulation, such as, for example, Na lauryl sulfate, fatty alcohol ether sulfates, di-Na N-lauryl-β-iminodipropionate, polyethoxylated castor oil or sorbitan monooleate, sorbitan monostearate, polysorbates (e.g. Tween), cetyl alcohol, lecithin, glyceryl monostearate, polyoxyethylene stearate, alkylphenol polyglycol ether, cetyltrimethylammonium chloride or mono/dialkylpolyglycol ether orthophosphoric acid monoethanolamine salts.

Stabilizers such as montmorillonites or colloidal silicas to stabilize emulsions or to prevent degradation of the active substances, such as antioxidants, for example tocopherols or butylated hydroxyanisole, or preservatives such as p-hydroxybenzoic esters, may likewise be necessary where appropriate to prepare the desired formulations. Preparations for parenteral administration may be present in separate dose unit forms such as, for example, ampoules or vials. Solutions of the active ingredient are preferably used, preferably aqueous solutions and especially isotonic solutions, but also suspensions. These injection forms can be made available as finished product or be prepared only immediately before use by mixing the active compound, e.g. the lyophilisate, where appropriate with further solid carriers, with the desired solvent or suspending agent.

Intranasal preparations may be in the form of aqueous or oily solutions or of aqueous or oily suspensions. They may also be in the form of lyophilisates which are prepared before use with the suitable solvent or suspending agent.

The manufacture, bottling and closure of the products takes place under the usual antimicrobial and aseptic conditions.

The invention further relates to processes for preparing the compounds of the invention.

The compounds of the general formula 1 with the meanings of $R^1$, $R^2$, $R^3$, $R^4$, $R^5$, $R^6$ and $R^7$ described above are prepared according to the invention

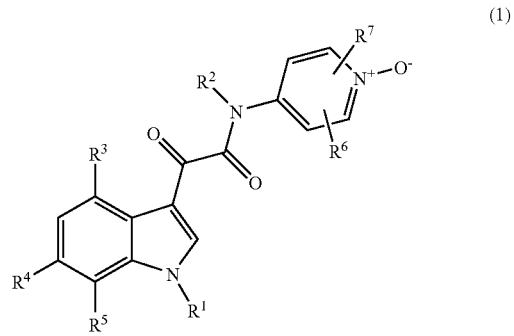

(1)

by oxidizing indol-3-ylglyoxylamides of the formula 2 having the same meaning of $R^1$, $R^2$, $R^6$ and $R^7$

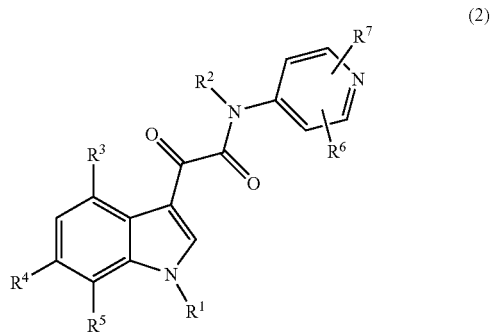

(2)

in which $R^3$, $R^4$ and $R^5$ are H or —$OR^8$, wherein at least one of these substituents must be —$OR^8$ and $R^8$ is a leaving group, e.g. alkyl, cycloalkyl, arylalkyl, acyl, alcoxycarbonyl, aryloxycarbonyl, aminocarbonyl, N-substituted aminocarbonyl, silyl and sulfonyl groups, and complexing agents such as compounds of boric acid or phosphoric acid, and covalently or co-ordinately bonded metals, such as zinc, aluminum or copper, in a manner known per se by treatment with an oxidizing agent, e.g. an organic peracid, preferably with m-chloroperbenzoic acid or/and peracetic acid, to the compounds of the invention of the formula 1 in which $R^3$, $R^4$ and $R^5$ are H or —$OR^8$, wherein at least one of these substituents must be —$OR^8$.

The compounds of the invention of the formula 1 are liberated by eliminating the leaving group $R^8$ still present in $R^3$ and/or $R^4$ and/or $R^5$.

The substituent —$R^8$ is eliminated by employing both acids and bases, such as, for example, hydrobromic acid, hydrochloric acid or hydriodic acid, or sodium hydroxide solution, potassium hydroxide solution, and sodium carbonate or potassium carbonate, but also activating Lewis acids such as, for example, $AlCl_3$, $BF_3$, $BBr_3$ or LiCl. The elimination reaction takes place in each case in the absence or presence of additional activators such as, for example, ethane-1,2-dithiol or benzyl mercaptan, and ether cleavages using hydrogen, under elevated pressure or atmospheric pressure, in the presence of a suitable catalyst such as, for example, palladium or iridium catalysts.

EXAMPLE

Example 1

Preparation of N-(3,5-Dichloro-1-oxopyridin-4-yl)-[1-(4-fluorobenzyl)-7-hydroxyindol-3-yl]glyoxylamide 12 g of N-(3,5-dichloropyridin-4-yl)-[7-benzyloxyl-(4-fluorobenzyl)-indol-3-yl]glyoxylamide are dissolved in 250 ml of methylene chloride. While stirring, a solution of 11.4 g of m-chloroperbenzoic acid (77%) in 30 ml of acetic acid is added dropwise. The mixture is stirred at room temperature for 7 days. The reaction mixture is adjusted to pH 8 by adding a saturated potassium carbonate solution. It is stirred vigorously for another hour. Then the phases are separated, and the organic phase is washed with 100 ml of water. The solvent is distilled out in vacuo. The residue is stirred with 50 ml of isopropanol. The crystals are removed and boiled with 50 ml of ethanol. The crystalline product is removed and dried.

Yield: 2.1 g (16.9% of theory) 1.8 g of the thus obtained N-(3,5-dichloro-1-oxopyridin-4-yl)-[7-benzyloxy-1-(4-fluorobenzyl)indol-3-yl]glyoxylamide are dissolved in 50 ml of dichloromethane. A solution of 0.7 ml of BBr$^3$ in 50 ml of dichloromethane is added dropwise while heating to reflux. The mixture is then stirred while heating to reflux for a further 3 hours. After cooling to 10° C., 50 ml of a 1M NaHCO$_3$ solution are added, thus resulting in a pH of 8–9. The temperature must be kept below 20° C. during this. The mixture is then stirred for 3 hours. The crystallized product is filtered off with suction, washed with water and dried. The crude product is recrystallized from ethanol.

Yield: 1.0 g (66.2% of theory) Melting point: 241–243° C.

Numerous further compounds of the formula 1 can be prepared by using the indicated process for preparation, of which the following are cited as examples:

The compounds of the invention are strong inhibitors of phosphodiesterase 4. Their therapeutic potential is demonstrated in vivo for example through the inhibition of the asthmatic late-phase reaction (eosinophilia) and through the inhibition of LPS-induced neutrophilia in rats.

Example 2

Phosphodiesterase 4 Inhibition

PDE4 activity is determined using enzyme preparations from human polymorphonuclear lymphocytes (PMNL). Human blood (buffy coats) was anticoagulated with citrate. A centrifugation at 700×g at room temperature (RT) for 20 minutes separates the platelet-rich plasma in the supernatant from the erythrocytes and leukocytes. The PMNLs for the PDE 4 determination are isolated by a subsequent dextran sedimentation and subsequent gradient centrifugation with Ficoll-Paque. After the cells have been washed twice, the erythrocytes which are still present are lysed by adding 10 ml of hypotonic buffer (155 mM NH$_4$Cl, 10 mM NaHCO$_3$, 0.1 mM EDTA, pH=7.4) at 4° C. within 6 minutes. The still intact PMNLs are then washed twice with PBS and lysed by ultrasound. The supernatant from a centrifugation at 4° C. and 48000×g for one hour contains the cytosolic fraction of PDE 4 and is employed for the PDE 4 measurements.

The phosphodiesterase activity is assayed using a modified Amersham Pharmacia Biotech method, an SPA (scintillation proximity assay).

The reaction mixtures contain buffer (50 mM Tris-HCl (pH 7.4), 5 mM MgCl$_2$, 100 μM cGMP), the inhibitors in variable concentrations and the appropriate enzyme preparation. The reaction is started by adding the substrate, 0.5 μM [$^3$H]-cAMP. The final volume is 100 μl. Test substances

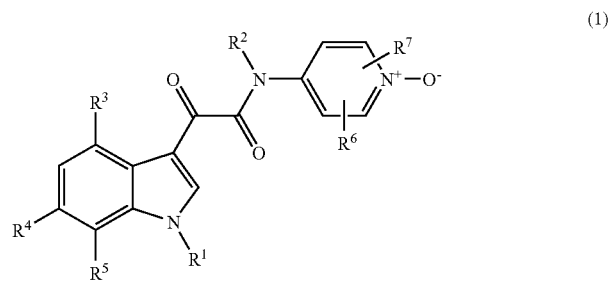

(1)

| Compound | —R$^1$ | —R$^2$ | —R$^3$ | —R$^4$ | —R$^5$ | —R$^6$ | —R$^7$ |
|---|---|---|---|---|---|---|---|
| 1 | 4-Fluorobenzyl- | —H | —H | —H | —OH | 3-Cl | 5-Cl |
| 2 | 4-Chlorobenzyl- | —H | —H | —H | —OH | 3-Cl | 5-Cl |
| 3 | 2-Chlorobenzyl- | —H | —H | —H | —OH | 3-Cl | 5-Cl |
| 4 | 2,4-Dichlorobenzyl | —H | —H | —H | —OH | 3-Cl | 5-Cl |
| 5 | 4-Fluorobenzyl- | —H | —H | —H | —OH | —H | —H |
| 6 | 4-Fluorobenzyl- | —H | —OH | —H | —H | 3-Cl | 5-Cl |
| 7 | 3-Nitrobenzyl- | —H | —H | —H | —OH | 3-Cl | 5-Cl |
| 8 | 2-Nitrobenzyl- | —H | —H | —H | —OH | 3-Cl | 5-Cl |
| 9 | 2,6-Difluorobenzyl- | —H | —H | —H | —OH | 3-Cl | 5-Cl |
| 10 | Isobutyl- | —H | —H | —H | —OH | 3-Cl | 5-Cl |
| 11 | Cyclopropyl-methyl | —H | —H | —H | —OH | 3-Cl | 5-Cl |
| 12 | 4-Hydroxybenzyl- | —H | —H | —H | —OH | 3-Cl | 5-Cl |
| 13 | 4-Fluorobenzyl- | —CH$_3$ | —H | —H | —OH | 3-Cl | 5-Cl |
| 14 | 4-Fluorobenzyl- | —H | —H | —OH | —H | 3-Cl | 5-Cl |
| 15 | 2-Chlorobenzyl- | —H | —H | —OH | —H | —H | —H | are made up as stock solutions in DMSO. The DMSO concentration in the reaction mixture is 1% v/v. The PDE activity is unaffected at this DMSO concentration. After the reaction has been started by adding substrate, the samples are incubated at 37° C. for 30 minutes. The reaction is stopped by adding a defined amount of SPA beads, and the samples are counted after one hour in a Beta counter. The nonspecific enzymic activity (the blank) is determined in the presence of 100 μM rolipram and subtracted from the test results. The incubation mixtures for the PDE4 assay contain 100 μM cGMP in order to inhibit any contamination by PDE 3.

The $IC_{50}$ values for inhibition of phosphodiesterase 4 determined for the compounds of the invention were in the range from $10^{-10}$ to $10^{-5}$ M. The selectivity factor in relation to PDE of types 3, 5 and 7 is from 100 to 10.000.

Example 3

Inhibition of Late-phase Eosinophilia 48 h after Inhalational Ovalbumin Challenge in Actively Sensitized Brown Norway Rats Inhibition of the pulmonary eosinophilic infiltration by the substances of the invention is tested on male brown Norway rats (200–250 g) actively sensitized against ovalbumin (OVA). The sensitization takes place by subcutaneous injections of a suspension of 10 μg of OVA together with 20 mg of aluminum hydroxide as adjuvant in 0.5 ml of physiological saline per animal on day 1, 14 and 21. In addition to this, the animals receive at the same time i.p. injections of 0.25 ml of *Bordetella pertussis* vaccine dilution per animal. On day 28 of the test, the animals are placed singly in open 1 l Plexiglas boxes connected to a head/nose exposure apparatus. The animals are exposed to an aerosol of 1.0% ovalbumin suspension (allergen challenge). The ovalbumin aerosol is generated by a nebulizer (Bird micro nebulizer, Palm Springs Calif., USA) operated with compressed air (0.2 MPa). The exposure time is 1 hour, with an aerosol of 0.9% saline being nebulized for normal controls likewise for 1 hour.

48 hours after the allergen challenge there is a massive migration of eosinophilic granulocytes into the lungs of the animals. At this time, the animals are anesthetized with an overdose of ethylurethane (1.5 g/kg of body weight i.p.), and a bronchoalveolar lavage (BAL) is carried out with 3×4 ml of Hank's balanced solution. The total cell count and the number of eosinophilic granulocytes in the pooled BAL liquid are subsequently determined using an automatic cell differentiation instrument (Bayer Diagnostics Technicon H1E). The eosinophils (EOS) in the BAL are calculated for each animal in $10^6$/animal: EOS/μl×BAL recovery (ml)=EOS/animal.

Two control groups (nebulization of physiological saline and nebulization of OVA solution) are included in each test.

The percentage inhibition of the eosinophilia in the test group treated with the substance is calculated by the following formula:

$$\{((OVAC-SC)-(OVAD-SC))/(OVAC-SC)\}\times 100\%=\% \text{ inhibition}$$

(SC=control group treated with vehicle and challenged with 0.9% saline; OVAC=control group treated with vehicle and challenged with 1% ovalbumin suspension; OVAD=test group treated with substance and challenged with 1% ovalbumin suspension)

The test substances are administered intraperitoneally or orally as suspension in 10% polyethylene glycol 300 and 0.5% 5-hydroxyethylcellulose 2 hours before the allergen challenge. The control groups are treated with the vehicle in accordance with the test substance application form.

The compounds of the invention inhibit the late-phase eosinophilia by 30% to 100% after intraperitoneal administration of 10 mg/kg and by 30% to 75% after oral administration of 30 mg/kg.

The compounds of the invention are thus particularly suitable for producing drug products for the treatment of disorders associated with the effect of eosinophils.

Example 4

Inhibition of Lipopolysaccharide (LPS)-induced Pulmonary Neutrophilia in Lewis Rats The inhibition of pulmonary neutrophil infiltration by the substances of the invention is tested on male Lewis rats (250–350 g). On the day of the test, the animals are placed singly in open 1 l Plexiglas boxes connected to a head/nose exposure apparatus. The animals are exposed to an aerosol from a lipopolysaccharide suspension (100 μg of LPS/ml of 0.1% hydroxylamine solution) in PBS (LSP provocation). The LPS/hydroxylamine aerosol is generated by a nebulizer (Bird micro nebulizer, Palm Springs Calif., USA) operated by compressed air (0.2 MPa). The exposure time is 40 minutes, with an aerosol being nebulized from 0.1% hydroxylamine solution in PBS for normal controls, likewise for 40 minutes.

6 hours after the LPS provocation there is a maximal, massive migration of neutrophilic granulocytes into the lungs of the animals. At this time, the animals are anesthetized with an overdose of ethylurethane (1.5 g/kg of body weight i.p.), and a bronchoalveolar lavage (BAL) is carried out with 3×4 ml of Hank's balanced solution. The total cell count and the number of neutrophilic granulocytes in the pooled BAL liquid are subsequently determined using an automatic cell differentiation apparatus (Bayer Diagnostics Technicon H1E). The neutrophils (NEUTRO) in the BAL are calculated for each animal in $10^6$/animal: NEUTRO/μl× BAL recovery (ml)=NEUTRO/animal.

Two control groups (nebulization of 0.1% hydroxylamine solution in PBS and nebulization of 100 μg of LPS/ml of 0.1% hydroxylamine solution in PBS) are included in each test.

The percentage inhibition of the neutrophilia in the test group treated with the substance is calculated by the following formula:

$$\{((LPSC-SC)-(LPSD-SC))/(LPSC-SC)\}\times 100\%=\% \text{ inhibition}$$

SC=control group treated with vehicle and challenged with 0.1% hydroxylamine solution; LPSC=control group treated with vehicle and challenged with LPS (100 μg/ml of 0.1% hydroxylamine solution); LPSD=test group treated with substance and challenged with LPS (100 μg/ml of 0.1% hydroxylamine solution).

The test substances are administered orally as suspension in 10% polyethylene glycol 300 and 0.5% 5-hydroxyethylcellulose 2 hours before the LPS provocation. The control groups are treated with the vehicle in accordance with the test substance administration form.

The compounds of the invention inhibit the neutrophilia by 30% to 90% after oral administration of 10 mg/kg and are thus particularly suitable for producing drug products for the treatment of disorders associated with the effect of neutrophils.

The invention claimed is:

1. A compound of formula 1

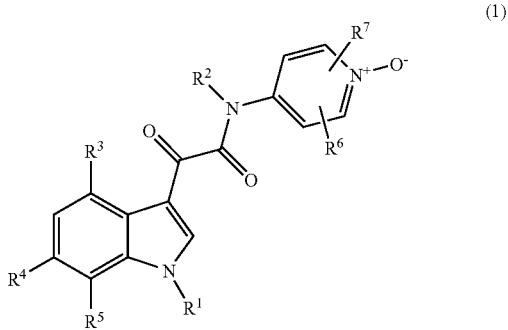

wherein
$R^1$
(i) is $-C_{1-10}$-alkyl, straight-chain or branched-chain, optionally mono- or polysubstituted by mono-, bi- or tricyclic saturated or mono- or polyunsaturated carbocycles with 3–14 ring members,
wherein the carbocyclic substituents in turn are substituted one or more times by $-NO_2$ and may optionally be substituted one or more times by $-C_{1-6}$-alkyl, $-OH$, $-NH_2$, $-NHC_{1-6}$-alkyl, $-N(C_{1-6}$-alkyl$)_2$, $-NO_2$, $-CN$, $-F$, $-Cl$, $-Br$, $-I$, $-O-C_{1-6}$-alkyl, $-S-C_{1-6}$-alkyl, $-SO_3H$, $-SO_2C_{1-6}$-alkyl, $-OSO_2C_{1-6}$-alkyl, $-COOH$, $-(CO)C_{1-5}$-alkyl, $-COO-C_{1-5}$-alkyl or/and $-O(CO)C_{1-5}$-alkyl, and wherein the alkyl groups on the carbocyclic substituents in turn may optionally be substituted one or more times by $-OH$, $-SH$, $-NH_2$, $-F$, $-Cl$, $-Br$, $-I$, $-SO_3H$ or/and $-COOH$,
$R^2$ is hydrogen or $-C_{1-3}$-alkyl,
$R^3$, $R^4$ and $R^5$ are hydrogen or a hydroxyl group, wherein at least one of these substituents must be a hydroxyl group,
$R^6$ and $R^7$ may be identical or different and are hydrogen, $-C_{1-6}$-alkyl, $-OH$, $-SH$, $-NH_2$, $-NHC_{1-6}$-alkyl, $-N(C_{1-6}$-alkyl$)_2$, $-NO_2$, $-CN$, $-SO_3H$, $-SO_3-C_{1-6}$-alkyl, $-COOH$, $-COO-C_{1-6}$-alkyl, $-O(CO)-C_{1-5}$-alkyl, $-F$, $-Cl$, $-Br$, $-I$, $-O-C_{1-6}$-alkyl, $-S-C_{1-6}$-alkyl, -phenyl or -pyridyl, wherein the phenyl or pyridyl substituents in turn may optionally be substituted one or more times by $-C_{1-3}$-alkyl, $-OH$, $-SH$, $-NH_2$, $-NHC_{1-3}$-alkyl, $-N(C_{1-3}$-alkyl$)_2$, $-NO_2$, $-CN$, $-SO_3H$, $-SO_3C_{1-3}$-alkyl, $-COOH$, $-COOC_{1-3}$-alkyl, $-F$, $-Cl$, $-Br$, $-I$, $-O-C_{1-3}$-alkyl, $-S-C_{1-3}$-alkyl, or/and $-O(CO)C_{1-3}$-alkyl, and wherein the alkyl substituents in turn may optionally be substituted one or more times by $-OH$, $-SH$, $-NH_2$, $-F$, $-Cl$, $-Br$, $-I$, $-SO_3H$, $-SO_3C_{1-3}$-alkyl, $-COOH$, $-COOC_{1-3}$-alkyl, $-O-C_{1-3}$-alkyl, $-S-C_{1-3}$-alkyl or/and $-O(CO)-C_{1-3}$-alkyl, or a salt of the compounds of formula 1.

2. A compound as claimed in claim 1 having at least one asymmetric carbon atom in the D form, the L form and D,L mixtures, and in the case of a plurality of asymmetric carbon atoms also the diastereomeric forms.

3. A compound as claimed in claim 1 wherein $R^2$ is hydrogen or a methyl group.

4. A compound as claimed in claim 1, wherein $R^3=-H$, $R^4=H$ and $R^5=-OH$.

5. A compound as claimed in claim 1, wherein at least one of $R^6$ and $R^7$ is a halogen atom.

6. A compound according to claim 1 selected from the group consisting of:

N-(3,5-dichloro-1-oxopyridin-4-yl)-[7-hydroxy-1-(3-nitrobenzyl)-indol-3-yl]glyoxylamide;

N-(3,5-dichloro-1-oxopyridin-4-yl)-[7-hydroxy-1-(2-nitrobenzyl)-indol-3-yl]glyoxylamide;

and physiologically tolerated salts thereof.

7. A composition comprising a compound of claim 1 and one or more conventional physiologically tolerated carrier, diluent and excipient.

* * * * *